US009063129B2

(12) United States Patent
Elsemore et al.

(10) Patent No.: US 9,063,129 B2
(45) Date of Patent: Jun. 23, 2015

(54) DEVICE, KIT AND METHOD FOR HOOKWORM ANTIGEN CAPTURE AND DETECTION

(75) Inventors: David Allen Elsemore, South Portland, ME (US); Laurie A. Flynn, Raymond, ME (US)

(73) Assignee: IDEXX Laboratories, Inc., Westbrook, ME (US)

(*) Notice: Subject to any disclaimer, the term of this patent is extended or adjusted under 35 U.S.C. 154(b) by 1218 days.

(21) Appl. No.: 11/763,583

(22) Filed: Jun. 15, 2007

(65) Prior Publication Data

US 2008/0311557 A1 Dec. 18, 2008

(51) Int. Cl.
*G01N 33/53* (2006.01)
(52) U.S. Cl.
CPC .................................. *G01N 33/5308* (2013.01)
(58) Field of Classification Search
None
See application file for complete search history.

(56) References Cited

U.S. PATENT DOCUMENTS

| | | | |
|---|---|---|---|
| 4,322,495 A | 3/1982 | Kato | |
| 4,756,908 A | 7/1988 | Lew | |
| 4,839,275 A | 6/1989 | Weil | |
| 4,978,504 A | 12/1990 | Nason | |
| 5,078,968 A | 1/1992 | Nason | |
| 5,238,649 A | 8/1993 | Nason | |
| 5,266,266 A | 11/1993 | Nason | |
| 5,726,010 A | 3/1998 | Clark | |
| 5,753,787 A | 5/1998 | Hawdon et al. | |
| 5,882,943 A | 3/1999 | Aldeen | |
| 6,057,166 A | 5/2000 | Childs et al. | |
| 6,391,569 B1 | 5/2002 | Grieve et al. | |
| 6,596,502 B2 * | 7/2003 | Lee | 435/7.22 |
| 7,303,752 B2 | 12/2007 | Hotez et al. | |
| 2002/0132270 A1 | 9/2002 | Lee | |
| 2003/0129680 A1 | 7/2003 | O'Connor | |
| 2004/0014087 A1 | 1/2004 | Hodgson et al. | |
| 2004/0214244 A1 | 10/2004 | Tonelli et al. | |
| 2005/0042232 A1 | 2/2005 | Hotez et al. | |
| 2006/0198844 A1 | 9/2006 | Langenfeld | |
| 2007/0053920 A1 | 3/2007 | Heath et al. | |
| 2008/0033148 A1 | 2/2008 | Xu et al. | |
| 2008/0108793 A1 | 5/2008 | Berman et al. | |
| 2008/0311600 A1 | 12/2008 | Elsemore et al. | |
| 2009/0286227 A1 | 11/2009 | Elsemore et al. | |
| 2009/0286228 A1 | 11/2009 | Elsemore et al. | |
| 2009/0286229 A1 | 11/2009 | Elsemore et al. | |
| 2009/0286230 A1 | 11/2009 | Elsemore et al. | |
| 2009/0286231 A1 | 11/2009 | Elsemore et al. | |

FOREIGN PATENT DOCUMENTS

| | | |
|---|---|---|
| WO | WO 98/12563 | 3/1998 |
| WO | WO 02/075313 | 9/2002 |
| WO | WO 03/032917 | 4/2003 |
| WO | WO 2004/097412 | 11/2004 |
| WO | WO 2006/135799 | 12/2006 |
| WO | WO 2008/156650 | 12/2008 |
| WO | WO 2009/143080 | 11/2009 |
| WO | WO 2009/143083 | 11/2009 |

OTHER PUBLICATIONS

Bungiro and Cappello, "Detection of Excretory/Secretory Coproantigens in Hookworm infection," (2005), Am. J. Trop. Med. Hyg. 73(5):915-920.
Hill et al., "A Trichuris specific diagnostic antigen from culture fluids of Trichuris suis adult worms," (1997), Veterinary Parasitology 68:91-102.
Yamasaki et al., "Development of Highly Specific Recombinant Toxocara canis Second-Stage Larva Excretory-Secretory Antigen for Immunodiagnosis of Human Toxocariasis," (2000), Journal of Clinical Microbiology 38(4):1409-1413.
Zhan et al., "Molecular characterisation of the Ancylostoma-secreted protein family from the adult stage of Ancylostoma caninum," (2003), International Journal for Parisitology 33:897-907.
Bungiro, Jr., et al., "Purification and Molecular Cloning of and Immunization with Ancylostoma ceylancium Excretory-Secretory Protein 2, an Immunoreactive Protein Produced by Adult Hookworms," (2004), Infection and Immunity 72(4):2203-2213.
Daub, et al. "A survey of genes expressed in adults of the human hookworm, *Necator americanus*", *Parasitology*, vol. 120, pp. 171-184, (2000).
Voller, "The Enzyme Linked Immunosorbent Assay", *Diagnostic Horizon*, vol. 2, No. 1, pp. 1-7, Feb. 1978.
Hotez, et al., "Pediatric Geohelminth Infections: Trichuriasis, Ascariasis, and Hookworm Infections", *Seminarsin Pediatric Infectious Diseases*, vol. 11, No. 5, pp. 236-244, (2000).
Jones, et al., "Hookworm infection: molecular mechanisms of disease and targets for control", *Drug Discovery Today: Disease Mechanisms*, vol. 1, No. 2, pp. 217-222, (2004).
Ambler, et al., "Biological Techniques for Studying the Allergenic Components of Nematodes. I. Detection of Allergenic Components in *Ascaris suum* Extracts", *J. Immunol. Methods*, vol. 1, No. 4, pp. 317-327, (1972).
Britton, et al., "Extensive diversity in repeat unit sequences of the cDNA encoding the polyprotein antigen/allergen from the bovine lungworm Dictyocaulus viviparous", *Mol. Biochem. Parasitol.* vol. 72, Nos. 1-2, pp. 77-88, (1995).

(Continued)

*Primary Examiner* — Patricia A Duffy
(74) *Attorney, Agent, or Firm* — McDonnell Boehnen Hulbert & Berghoff LLP

(57) ABSTRACT

A device, kit and method for detecting the presence or absence of hookworm antigens. The device, kit and method of the present invention may be used to confirm the presence or absence of hookworm in a fecal sample that may be infected with one or more of roundworm, whipworm, tapeworm and heartworm, and whether or not hookworm ova are present in the sample. Further, the device, kit and method of the present invention may be used to confirm the presence or absence of hookworm in a fecal sample excreted by a canine animal as early as nine days after the animal first becomes infected with hookworm.

13 Claims, 8 Drawing Sheets

(56) References Cited

OTHER PUBLICATIONS

Christie, et al., "The ABA-1 allergen of the nematode *Ascaris suum*: epitope stability, mass spectrometry, and N-terminal sequence comparison with its homologue in *Toxocara canis*", *Clin. Exp. Immunol.*, vol. 92, pp. 125-132, (1993).
Kennedy, "Stage-specific secreted antigens of the parasitic larval stages of the nematode *Ascaris*" *Immunology*, vol. 58, No. 3, pp. 515-522, (1986).
McGibbon, et al., "Identification of the major *Ascaris* allergen and its purification to homogeneity by high-performance liquid chromatography", *Mol. Biochem. Parasitol.*, vol. 39, No. 2, pp. 163-171, (1990).
Meenan, et al., "Resonance assignment of ABA-1A, from *Ascaris suum* nematode polyprotein allergen", *J. Biomol. NMR*, vol. 32, No. 2 p. 176, (2005).
Poole, et al., "Cloning of a cuticular antigen that contains multiple tandem repeats from the filarial parasite *Dirofilaria immitis*", *Proc. Natl. Acad. Sci. USA*, vol. 89, No. 13, pp. 5986-5990, (1992).
Solovyova, et al., "The polyprotein and FAR lipid binding proteins of nematodes: shape and monomer/dimer states in ligand-free and bound forms", *Eur. Biophys. J.*, vol. 32, No. 5, pp. 465-476, (2003).
Spence, et al., "A cDNA encoding repeating units of the ABA-1 allergen of *Ascaris*", *Mol. Biochem. Parasitol.* vol. 57, pp. 339-343, (1993).
The *C. elegans* consortium, et al., "Genome Sequence of the Nematode *C. elegans*: A Platform for Investigating Biology", *Science*, vol. 282, pp. 2012-2018, (1998).
Tweedie, et al., "*Brugia pahangi* and *Brugia malayi*: a surface-associated glycoprotein (gp15/400) is composed of multiple tandemly repeated units and processed from a 400-kDa precursor", *Exp. Parasitol.*, vol. 76, No. 2, pp. 156-164, (1993).
Bailey, "The Raising of a Polyclonal Antiserum to a Protein", *Methods Mol. Biol.*, vol. 32, pp. 381-388, (1994).
Barker, et al., "Isolation of a gene family that encodes the porin-like proteins from the human parasitic nematode *Trichuris trichiura*", *Gene*, vol. 229, pp. 131-136, (1999).
Dean, "Preparation and Characterization of Monoclonal Antibodies to Proteins and Other Cellular Components", *Methods Mol. Biol.*, vol. 32, pp. 361-379, (1994).
Dean, "Preparation and Testing of Monoclonal Antibodies to Recombinant Proteins", *Methods Mol. Biol.*, vol. 80, pp. 23-37, (1998).
Drenckhanhn, et al., "Production of Polyclonal Antibodies against Proteins and Peptides", *Methods Cell Biol.*, vol. 37, pp. 7-56, (1993).
Dryden, et al., "Comparison of Common Fecal Flotation Techniques for the Recovery of Parasite Eggs and Oocysts", *Vet. Ther.*, vol. 6, No. 1, pp. 15-28, (2005).
Gullick. "Production of Antisera to Synthetic Peptides", *Methods Mol. Biol.*, vol. 32. pp. 389-399, (1994).
Kennedy, "The Nematode Polyprotein Allergens/Antigens", *Parasitol. Today*, vol. 16, No. 9, pp. 373-380, (2000).
Memoranda, "Parasite Antigens", *Bull. World Health Organ*, vol. 52, pp. 237-249, (1975).
Morrison, "In Vitro Antibodies: Strategies for Production and Application", *Annu. Rev. Immunol.*, vol. 10, pp. 239-265, (1992).
Prociv et al., "Human enteric infection with *Ancyostoma caninum*: hookworms reappraised in the light of a "new" zoonosis", *Acta. Tropica.*, vol. 62, pp. 23-44, (1996).
Wright, et al., "Genetically Engineered Antibodies: Progress and Prospects", *Crit. Rev. Immunol.*, vol. 12 (3-4), pp. 125-168, (1992).
Xia, et al., "The ABA-1 allergen of *Ascaris lumbricoides*: sequence polymorphism stage and tissue-specific expression, lipid binding function and protein biophysical properties", *Parasitology*, vol. 120 (Pt.2), pp. 211-224, (2000).
Yahiro, et al., "Identification, characterization and expression of *Toxocara canis* nematode polyprotein allergen TBA-1", *Parasite Immunol.*, vol. 20, No. 8, pp. 351-357, (1998).
Babin, et al., "The Isoinhibitors of Chymotrypsin/Elastase from *Ascaris lumbricoides*: The Primary Structure", *Archives of Biochemistry and Biophysics*, vol. 232, No. 1, pp. 143-161, (1984).

Cappello, et al., "*Ancylostoma caninum* anticoagulant peptide: A hookworm-derived inhibitor of human coagulation factor Xa", *Proc. Natl. Acad. Sci.*, vol. 92, pp. 6152-1656, (1995).
Ford, et al., "Characterization of a Novel Filarial Serine Protease Inhibitor, Ov-SPI-1, from *Onchocerca volvulus*, with Potential Multifunctional Roles during Development of the Parasite", *J. of Biol. Chem.*, vol. 280, No. 49, pp. 40845-40856, (2005).
Fraefel, et al., "The amino acid sequence of a trypsin inhibitor isolated from *Ascaris* (*Ascaris lumbricoides* var. suum)", *Biochim. Biophys. Acta*, vol. 154, pp. 615-617, (1968).
Goodman, et al., "Isolation of the Trypsin Inhibitors in *Ascaris lumbricoides* var. suum Using Affinity Chromatography", *Analytical Biochemistry*, vol. 120, pp. 387-393 (1982).
Grasberger, et al., "High-resolution structure of *Ascaris* trypsin inhibitor in solution: direct evidence for a pH-induced conformational transition in the reactive site", *Structure*, vol. 2, No. 7, pp. 669-678, (1994).
Gronenborn, et al., "Sequential resonance assignment and secondary structure determination of the *Ascaris* trypsin inhibitor, a member of a novel class of proteinase inhibitors", *Biochemistry*, vol. 29, No. 1, pp. 183-189, (1990).
Harrison, et al., "Molecular Characterization of *Ancylostoma* Inhibitors of Coagulation Factor Xa", *J. of Biol. Chem.*, vol. 277, No. 8, pp. 6223-6229, (2002).
Hawley, et al., "*Ascaris suum*: Are Trypsin Inhibitors Involved in Species Specificity of Ascarid Nematodes?", *Experimental Parasitology*, vol. 75, pp. 112-118 (1992).
Huang, et al., "The molecular structure of the complex of *Ascaris* chymotrypsin/elastase inhibitor with porcine elastase", *Structure*, vol. 2, No. 7, pp. 679-689, (1994).
Lu, et al., "*Anisakis simplex*: Mutational Bursts in the Reactive Site Centers of Serine Protease Inhibitors from an Ascarid Nematode", *Experimental Parasitology*, vol. 89, pp. 257-261, (1998).
Martzen, et al., "*Ascaris suum*: Localization by Immunochemical and Fluorescent Probes of Host Proteases and Parasite Proteinase Inhibitors in Cross-sections", *Experimental Parasitology*, vol. 60, pp. 139-149, (1985).
Nguyen, et al., "Expression and characterization of elastase inhibitors from the ascarid nematodes *Anisakis simplex* and *Ascaris suum*", *Mol. Biochem. Parasitology*, vol. 102, pp. 79-89, (1999).
Peanasky, et al., "The Isoinhibitors of Chymotrypsin/Elastase from *Ascaris lumbricoides*: Isolation by Affinity Chromatography and Association with the Enzymes", *Archives of Biochemistry and Biophysics*, vol. 232, No. 1, pp. 127-134, (1984).
Rhoads, et al., "*Trichuris suis*: A Secretory Serine Protease Inhibitor", *Experimental Parasitology*, vol. 94, pp. 1-7, (2000).
Rhoads, et al., "*Trichuris suis*: A Secretory Chymotrypsin/Elastase Inhibitor with Potential as an Immunomodulator", *Experimental Parasitology*, vol. 95, pp. 36-44, (2000).
Stanssens, et al., "Anticoagulant repertoire of the hookworm *Ancylostoma canium*", *Proc. Natl. Acad. Sci.*, vol. 93, pp. 2149-2154, (1996).
Uniprot submission P07851. Aug. 1988. [Retrieved from the internet Dec. 13, 2009: ,URL:http://www.uniprot.org/uniprot/P07851.] in entirety.
Westermarck, et al., "Faecal hydrolase activity as determined by radial enzyme diffusion: a new method for detecting pancreatic dysfunction in the dog", *Res. Vet. Sci.*, vol. 28, No. 3, pp. 341-346, (1980) (Abstract).
Williams, et al., "Comparison of methods for assay of the fecal proteolytic activity", *Vet. Clin. Pathol.*, vol. 19, No. 1, pp. 20-24, (1990) (Abstract).
Williams, et al., "Fecal proteolytic activity in clinically normal cats and in a cat with exocrine pancreatic insufficiency", *J. Am. Vet. Med. Assoc.*, vol. 197, No. 2, pp. 1112-1113, 1116, (1990) (Abstract).
Uniprot Submission P918l1. May 1997 [Retrieved from the internet Nov. 7, 2009: [URL:http://www.uniprot.org/uniprot/P918111].
Uniport submission O44397. Jun. 1988 [Retrieved from the internet Nov. 11, 2009: [<URL:http://www.uniport.org/uniport/O44397>].
U.S. Appl. No. 12/467,778, filed May 18, 2009, Elsemore, et al.
Allan, et al., "Coproantigen detection for immunodiagnosis of echinococcosis and taeniasis in dogs and humans", *Parasitology*, 1992, 104:347-355.

(56) References Cited

OTHER PUBLICATIONS

Barker, et al., "Isolation of a gene family that encodes the porin-like proteins from the human parasitic nematode *Trichuris trichiura*", Gene, 1999, 229:131-136.

Bethony, et al., "Antibodies against a secreted protein from hookworm larvae reduce the intensity of hookworm infection in humans and vaccinated laboratory animals", *FASEB Journal*, 2005, 19:1743-1745.

Bungiro, et al., "Detection of excretory/secretory coproantigens in experimental hookworm infection", *Am. J. Trop. Med. Hyg.*, 2005, 73(5):915-920.

Bungiro, et al., "Purification and molecular cloning of and immunization with *Ancylostoma ceylanicum* excretory-secretory protein 2, an immunoreactive protein produced by adult hookworms", *Infection and Immunity*, 2004, 72(4):2203-2213.

Croese, et al., "Occult enteric infection by *Ancylostoma caninum*: A previously unrecognized zoonosis", *Gastroenterology*, 1994, 106:3-12.

Daub, et al., "A survey of genes expressed in adults of the human hookworm, Nacator americanus", *Parasitology*, 2000, 120:171-184.

De Oliveira Vasconcelos, et al., "Identification of stage-specific proteins of *Angiostrongylus vasorum* (Baillet, 1866) Kamensky", *Parasitol. Res.*, 2007, 102(3):389-395.

Drake, et al., "Molecular and functional characterization of a recombinant protein of *Trichuris trichiura*", *Proc. Bio. Sci.*, 1998, 265:1559-1565.

Drake, et al., "The major secreted product of the whipworm, *Trichuris*, is a pore-forming protein", *Proc. Bio. Sci*, 1994, 257:255-261.

Gasser, et al., "Improved molecular diagnostic tools for human hookworms", *Expert Rev. Mol. Diagn.*, 2009, 9(1):17-21.

Jenkins et al., "Functional antigens of *Trichuris muris* released during in vitro maintenance: their immunogenicity and partial purification", *Parasitology*, 1983, 86:73-82.

Johnson, et al., "Detection of gastrointestinal nematodes by a coproantigen capture ELISA", *Res. Vet. Sci.*, 1996, 60:7-12.

Kania et al., "*Anoplocephala perfoliata* coproantigen detection: a preliminary study", *Vet. Parasitol.*, 2005, 127(2): 115-119.

Lillywhite et al., "Humoral immune responses in human infection with the whipworm *Trichuris trichiura*", *Parasite Immunol.*, 1991, 13:491-507.

Lillywhite et al., "Identification and characterization of excreted/secreted products of *Trichuris trichiura*", *Parasite Immunol.*, 1995, 17:47-54.

Nukumi et al., "Whey acidic protein (WAP) regulates the proliferation of mammary epithelial cells by preventing serine protease from degrading laminin", *J. Cell. Physiol.*, May 31, 2007, 213:793-800.

Parkinson et al., "400 000 nematode ESTs on the Net", *Trends Parasitol.*, Jul. 2003, 19(7):283-286.

Song et al., "Cross-reactivity between sera from dogs experimentally infected with *Dirofilaria immitis* and crude extract of *Toxocara canis*", *Korean J. Parasitol.*, Dec. 2002, 40(4):195-198.

Traub, et al., "Canine gastrointestinal parasitic zoonoses in India", *Trends in Parasit.*, 2005, 21(1):42-48.

Wakelin, "Acquired immunity to *Trichuris muris* in the albino laboratory mouse", *Parasitology*, 1967, 57:515-524.

GenBank Accession No. AAD01628.1. Jan. 1999. [Retrieved from the Internet Feb. 25, 2010: <URL:http://ncbi.nlm.nih.gov/protein/410955>].

GenBank Accession No. BM965689.1. Mar. 2002. [Retrieved from the Internet Feb. 25, 2010: <URL:http://ncbi.nlm.nih.gov/nucest/19558140>].

GenBank Accession No. BQ088667.1. Apr. 2002. [Retrieved from the Internet Feb. 25, 2010: <URL:http://ncbi.nlm.nih.gov/nucest/20062868>].

GenBank Accession No. AAC17174.1. May 1998. [Retrieved from the Internet Feb. 25, 2010: <URL:http://ncbi.nlm.nih.gov/protein/3152922>].

GenBank Accession No. AAC47345.1. Oct. 2007. [Retrieved from the Internet Feb. 25, 2010: <URL:http://ncbi.nlm.nih.gov/protein/1663728>].

GenBank Accession No. AAG31482.1. Nov. 2000. [Retrieved from the Internet Feb. 25, 2010: <URL:http://ncbi.nlm.nih.gov/protein/11138792>].

GenBank Accession No. NP_510821. Nov. 2008. [Retrieved from the Internet Feb. 25, 2010: <URL:http://ncbi.nlm.nih.gov/protein/17551598>].

GenBank Accession No. CB098869. Jan. 28, 2003. [Retrieved from the Internet Mar. 30, 2010: <URL:http://ncbi.nlm.nih.gov/nucest/27924676>].

GenBank Accession No. CB099165. Jan. 28, 2003. [Retrieved from the Internet Mar. 30, 2010: <URL:http://ncbi.nlm.nih.gov/nucest/27924972>].

GenBank Accession No. CB099244. Jan. 28, 2003. [Retrieved from the Internet Mar. 30, 2010: <URL:http://ncbi.nlm.nih.gov/nucest/27925051>].

GenBank Accession No. CB099367. Jan. 28, 2003. [Retrieved from the Internet Mar. 30, 2010: <URL:http://ncbi.nlm.nih.gov/nucest/27925174>].

GenBank Accession No. CB188155. Feb. 5, 2003. [Retrieved from the Internet Mar. 30, 2010: <URL:http://ncbi.nlm.nih.gov/nucest/28251547>].

GenBank Accession No. CB188174. Feb. 5, 2003. [Retrieved from the Internet Mar. 30, 2010: <URL:http://ncbi.nlm.nih.gov/nucest/28251566>].

GenBank Accession No. CB188239. Feb. 5, 2003. [Retrieved from the Internet Mar. 30, 2010: <URL:http://ncbi.nlm.nih.gov/nucest/28251631>].

GenBank Accession No. CB188637. Feb. 5, 2003. [Retrieved from the Internet Mar. 30, 2010: <URL:http://ncbi.nlm.nih.gov/nucest/28252029>].

GenBank Accession No. CB189034. Feb. 5, 2003. [Retrieved from the Internet Mar. 30, 2010: <URL:http://ncbi.nlm.nih.gov/nucest/28252426>].

GenBank Accession No. CB189036. Feb. 5, 2003. [Retrieved from the Internet Mar. 30, 2010: <URL:http://ncbi.nlm.nih.gov/nucest/28252428>].

GenBank Accession No. CB189116. Feb. 5, 2003. [Retrieved from the Internet Mar. 30, 2010: <URL:http://ncbi.nlm.nih.gov/nucest/28252508>].

GenBank Accession No. CB189285. Feb. 5, 2003. [Retrieved from the Internet Mar. 30, 2010: <URL:http://ncbi.nlm.nih.gov/nucest/28252677>].

GenBank Accession No. CB189434. Feb. 5, 2003. [Retrieved from the Internet Mar. 30, 2010: <URL:http://ncbi.nlm.nih.gov/nucest/28252826>].

GenBank Accession No. CB277501. Feb. 25, 2003. [Retrieved from the Internet Mar. 30, 2010: <URL:http://ncbi.nlm.nih.gov/nucest/28561086>].

GenBank Accession No. CB277590. Feb. 25, 2003. [Retrieved from the Internet Mar. 30, 2010: <URL:http://ncbi.nlm.nih.gov/nucest/28561175>].

GenBank Accession No. CB277641. Feb. 25, 2003. [Retrieved from the Internet Mar. 30, 2010: <URL:http://ncbi.nlm.nih.gov/nucest/28561226>].

GenBank Accession No. CB277653. Feb. 25, 2003. [Retrieved from the Internet Mar. 30, 2010: <URL:http://ncbi.nlm.nih.gov/nucest/28561238>].

GenBank Accession No. CB277950. Feb. 25, 2003. [Retrieved from the Internet Mar. 30, 2010: <URL:http://ncbi.nlm.nih.gov/nucest/28561535>].

GenBank Accession No. CB188241. Feb. 5, 2003. [Retrieved from the Internet Mar. 30, 2010: <URL:http://ncbi.nlm.nih.gov/nucest/28251633>].

GenBank Accession No. CB277846. Feb. 25, 2003. [Retrieved from the Internet Mar. 30, 2010: <URL:http://ncbi.nlm.nih.gov/nucest/28561431>].

GenBank Accession No. CB277826. Feb. 25, 2003. [Retrieved from the Internet Mar. 30, 2010: <URL:http://ncbi.nlm.nih.gov/nucest/28561411>].

(56) References Cited

OTHER PUBLICATIONS

GenBank Accession No. CB189366. Feb. 5, 2003. [Retrieved from the Internet Mar. 30, 2010: <URL:http://ncbi.nlm.nih.gov/nucest/28252758>].
GenBank Accession No. CB098807. Jan. 28, 2003. [Retrieved from the Internet Mar. 30, 2010: <URL:http://ncbi.nlm.nih.gov/nucest/27924614>].
GenBank Accession No. CB189370. Feb. 5, 2003. [Retrieved from the Internet Mar. 30, 2010: <URL:http://ncbi.nlm.nih.gov/nucest/28252762>].
GenBank Accession No. BQ089025. Apr. 5, 2002. [Retrieved from the Internet Mar. 30, 2010: <URL:http://ncbi.nlm.nih.gov/nucest/20063226>].
GenBank Accession No. BM966041. Mar. 20, 2002. [Retrieved from the Internet Mar. 30, 2010: <URL:http://ncbi.nlm.nih.gov/nucest/19558790>].
GenBank Accession No. BQ088880. Apr. 5, 2002. [Retrieved from the Internet Mar. 30, 2010: <URL:http://ncbi.nlm.nih.gov/nucest/20063081>].
Uniprot submission P07852. Aug. 1988. [Retrieved from the Internet Mar. 30, 2010: <URL: http://www.uniprot.org/uniprot/P07852>].
Uniprot submission Q06811. Nov. 1997. [Retrieved from the Internet Feb. 25, 2010: <URL://www.uniprot.org/uniprot/Q06811>].
Uniprot submission Q24702. Nov. 1996. [Retrieved from the Internet Feb. 25, 2010: <URL:http://uniprot.org/uniprot/Q24702>].
Uniprot submission P91811. May 1997. [Retrieved from the Internet Feb. 25, 2010: <URL:http://uniprot.org/uniprot/P91811>].
Uniprot submission O44397. Jun. 1988. [Retrieved from the Internet Nov. 11, 2009: <URL:http://uniprot.org/uniprot/O44397>].
Uniprot submission P19398. Nov. 1, 1990. [Retrieved from the Internet Mar. 30, 2010: <URL: http://www.uniprot.org/uniprot/P19398>].
Uniprot submission O77416. Nov. 1, 1998. [Retrieved from the Internet Mar. 30, 2010: <URL: http://www.uniprot.org/uniprot/O77416>].
Uniprot submission Q2VMT7. Jan. 10, 2006. [Retrieved from the Internet Mar. 30, 2010: <URL: http://www.uniprot.org/uniprot/Q2VMT7>].
Uniprot submission Q9U6V1. May 1, 2000. [Retrieved from the Internet Mar. 30, 2010: <URL: http://www.uniprot.org/uniprot/Q9U6V1>].
Uniprot submission Q16938. Nov. 1, 1996. [Retrieved from the Internet Mar. 30, 2010: <URL: http://www.uniprot.org/uniprot/Q16938>].
Uniprot submission Q962V8. Dec. 1, 2001. [Retrieved from the Internet Mar. 30, 2010: <URL: http://www.uniprot.org/uniprot/Q962V8>].
NCBI Blast: SEQ ID No. 4 (Performed Aug. 27, 2009 using http://blast.ncbi.nlm.nih.gov/blast.cgi).
Coulaud, J.P., et al., Albendazole: a new single dose anthelmintic. Study in 1455 patients, Acta Tropica 41:87-90 (1984).
IDEXX Laboratories Canine Paravovirus Antigen Test Kit package insert.
Deplazes et al., Detection of *Taenia hydatigena* copra-antigens by ELISA in dogs, Veterinary Parisitology 36:91-103 (1990).
Ott et al., Demonstration of both immunologically unique and common antigenic determinants in *Dirofilaria immitis* and *Toxocara canis* using monoclonal antibodies, Veterinary Immunology and Immunopathology 10:147-153 (1985).
Abdel-Rahman et al., Evaluation of a diagnostic monoclonal antibody-based capture enzyme-linked immunosorbent assay for detection of a 26- to 28-kd *Fasciola hepatica* coproantigen in cattle, American Journal of Veterinary Research 59:533-537 (1998).
Martinez-Maya et al., Taeniosis and detection of antibodies against Cysticeri among inhabitants of a rural community in Guerro State, Mexico, Salud Publica de Mexico 45:84-89 (2003).
Dumenigo et al., Kinetics of antibody-based antigen detection in serum and faeces of sheep experimentally infected with *Fasciola hepatica*, Veterinary Parisitology 86:23-31 (1999).
Willard et al., Diagnosis of Aelurostrongylus abstrusus and *Dirofilaria immitis* infections in cats from a human shelter, Journal of the American Veterinary Medical Association 192:913-916 (1988).
De Oliveira et al., IgM-ELISA for diagnosis of *Schistosomiasis mansoni* in low endemic areas, Cadernos de saúde de pública / Ministério da Saúde, Fundação Oswaldo Cruz, Escola Nacional de Saúde Pública 19:255-261 (2003).
Southworth, Exine development in *Gerbera jamesonii* (Asteraceae: Mutisieae), American Journal of Botany 70:1038-1047 (1983).
Carleton et al., Prevalence of *Dirofilaria immitis* and gastrointestinal helminths in cats euthanized at animal control agencies in northwest Georgia, Veterinary Parisitology 119:319-326 (2004).
Foreyt, W.J., Veterinary Parasitology Reference Manual, Fifth Edition, 2001, ISBN 0-8138-2419-2.
Roberts, L.S., et al., Foundations of Parasitology, Fifth Edition, 1996, Library of Congress Card Catalog No. 94-72939, ISBN 0-687-26071-S.

* cited by examiner

DEVICE, KIT AND METHOD FOR HOOKWORM ANTIGEN CAPTURE AND DETECTION

BACKGROUND OF THE INVENTION

1. Field of the Invention

The present invention relates to devices, kits and methods for the detection of hookworm in animals. More particularly, the invention relates to antibody-based devices, kits and methods for capturing and detecting hookworm antigens in an animal's feces for the purpose of diagnosing that animal as having or not having a hookworm infection. Even more particularly, the invention relates to antibody-based devices, kits and methods for diagnosing a hookworm infection in an animal before or after hookworm ova first appear in the animal's feces. Still more particularly, the invention relates to antibody-based devices, kits and methods for confirming the presence or absence of a hookworm infection in an animal regardless of whether that animal is infected with one or more of roundworm, whipworm, tapeworm and heartworm.

2. Description of the Prior Art

Hookworms are bloodsucking intestinal parasites that can cause their host to suffer serious illness, such as anemia, wasting and retarded development. For example, the hookworm *Ancylostoma caninum* causes significant disease in both dogs and humans (Prociv et al., Acta Trop. 1996 September; 62(1):23-44). Diagnosis of a hookworm infection typically is performed by following the fecal flotation method, which involves obtaining a fecal sample from the animal being diagnosed and visually inspecting it by microscope for hookworm ova. This microscopic diagnosis method, however, is time consuming and requires specialized equipment. Further, the accuracy of diagnosis using this method is highly dependent upon the skill and expertise of the clinician performing the inspection. (For example, a novice eye often will mistake ova of other parasitic nematodes for those of hookworm and vice versa.) This potential for misdiagnosis is unfortunate because a misdiagnosed animal may be given a treatment that is ineffective against hookworm, and therefore one that would not alleviate the animal's suffering or stop the progressive wasting of its health.

Another significant limitation of diagnosis by microscopic detection of ova is that because hookworm eggs generally are not detectable in host feces until well after infection manifests, it does not allow for early detection of hookworm infection. For example, hookworm ova generally do not appear in canine feces until about 17 days after oral ingestion of the parasite by the canine. This is a problem because symptoms such as severe weight loss and bloody diarrhea often distress the host before hookworm ova first appear in the feces. Early detection therefore is highly desirable.

For these reasons, there remains great potential for the development of a device, kit and method which can be used to correctly diagnose an animal as having or not having a hookworm infection, specifically, as opposed to a nematode infection, generally. There also remains great potential for such a device and method that can be used to make this diagnosis soon after the animal becomes infected. Further, it is desirable to have such a device and method suitable to detect hookworm in an animal sample that is easily obtainable. A particularly convenient sample is feces because unlike blood, for example, feces are readily excreted by animals. The ability to use an animal sample that is easily obtained would obviate the need to transport the animal, which in some cases may be too sick to travel, to a veterinary professional for sample collection, such as may be needed when blood, for example, must be collected.

Given that the needed device, kit and method should be able to detect the presence or confirm the absence of hookworm in an animal whether or not hookworm organisms, including hookworm ova, are in the test sample taken from the animal, the device and method should be aimed at the molecular level. In particular, the device, kit and method may be an antibody-based device and method which are capable of detecting the presence or absence of hookworm-specific antigens. While antibody-based strategies for detecting nematode antigens generally exist, none specifically have allowed the early detection of, or confirmation of the absence of, hookworm in a fecal sample from an animal that may also be infected by one or more of roundworm, whipworm, tapeworm and heartworm.

What is needed therefore is a device, kit and method for testing a fecal sample from an animal to determine whether the animal is infected with hookworm. The needed device, kit and method further should be able to specifically detect the presence or absence of hookworm in an animal whether or not hookworm ova are present in the animal's feces. Even further, the needed device, kit and method should be able to specifically detect hookworm in a fecal sample that may also include one or more of roundworm, whipworm, tapeworm and heartworm.

SUMMARY OF THE INVENTION

The present invention is based in part on the discovery of unexpected properties of a polyclonal antibody. Specifically, it was determined that a polyclonal antibody raised against hookworm *Ancylostoma caninum*-secreted protein-5 (ASP5) can be used to capture and detect the presence of hookworm coproantigens in a canine animal as early as between nine days and 13 days after the canine becomes infected with hookworm. Prior to the present invention it has been unknown whether any proteins of adult parasitic nematodes appear in a canine host's feces prior to the appearance of nematode ova. The ability of the present invention to detect ASP5 protein so quickly after infection is introduced to the host is interesting because it means that the hookworm coproantigens recognized by the polyclonal antibody appear in the host's feces before any whole hookworm, including hookworm ova, appear in the feces.

Further, it was determined that the same polyclonal antibody can be used to capture and detect the presence or absence of hookworm coproantigens in animals that are also infested by one or more of roundworm, whipworm, tapeworm and heartworm. This specificity for hookworm is surprising because hookworms, roundworms, whipworms, and heartworms all are related nematodes, and a polyclonal antibody raised against a particular protein of any one of these worms would be expected to crossreact with one or more of the other worms. The invention includes assay conditions under which this polyclonal antibody can be used to specifically capture and detect the presence or absence of hookworm coproantigens in animals, including in animals also infested by one or more of roundworm, whipworm, tapeworm and heartworm.

The invention, in one aspect, is a device for detecting the presence or absence of hookworm coproantigen. The invention further provides such a device for detecting the presence or absence of hookworm coproantigen in a mammal that is infected with one or more of roundworm, whipworm, tapeworm and heartworm. In one aspect of the invention, the device includes a solid support, wherein one or more polyclonal antibodies specific for the hookworm protein ASP5 are immobilized on the solid support.

In certain aspects of the invention, the device of the invention includes a lateral flow immunoassay device. In other aspects of the invention, the device of the invention includes an enzyme-linked immunosorbent assay (ELISA) device.

The invention includes a method for detecting the presence or absence of hookworm coproantigen. The method includes applying a fecal sample to the antibodies specific for hookworm ASP5 protein and capturing and detecting the presence or absence of ASP5 in that fecal sample. The detection step may include the detection of the presence or absence of an antigen/antibody complex. The method may further involve providing a second antibody that binds to the antigen of the antigen/antibody complex.

The invention further includes assay kits for detecting hookworm coproantigen. A kit therefore may include one or more devices of the present invention. For example, the kit may include anti-hookworm antibodies and means for determining binding of the antibodies to hookworm antigens in the sample. In one particular example, such a kit includes the device having an immobilized anti-hookworm antibody, one or more antigen capture reagents (e.g., a non-immobilized labeled antigen capture reagent and an immobilized antigen capture reagent) and wash reagent, as well as detector reagent and positive and negative control reagents, if desired or appropriate. Other components such as buffers, controls, and the like, may be included in such test kits. A kit may further include instructions for carrying out one or more methods of the present invention, including instructions for using any device of the present invention that is included with the kit.

DETAILED DESCRIPTION OF THE PREFERRED EMBODIMENT

The present invention, in one aspect, is a device for the diagnosis of hookworm infection in an animal, such as a mammal. The device therefore may be used to diagnose hookworm infection in a canine or feline, for example. In one aspect of the invention, the device uses anti-Ac-ASP-5 pAB to detect the presence or absence of hookworm in a fecal sample from the animal. It is to be understood, however, that the device is not limited to being used to detect the presence or absence of hookworm in a fecal sample. Therefore, the device may be used to detect the presence or absence of hookworm in, for example, a blood sample. When the device is used to detect the presence or absence of hookworm in a fecal sample, the device specifically confirms the presence or absence of hookworm even when the sample includes coproantigens from one or more of roundworm, whipworm, tapeworm and heartworm. In one aspect of the invention, the device includes a solid support, wherein anti-Ac-ASP-5 pAB is immobilized on the solid support.

Figure 1A:
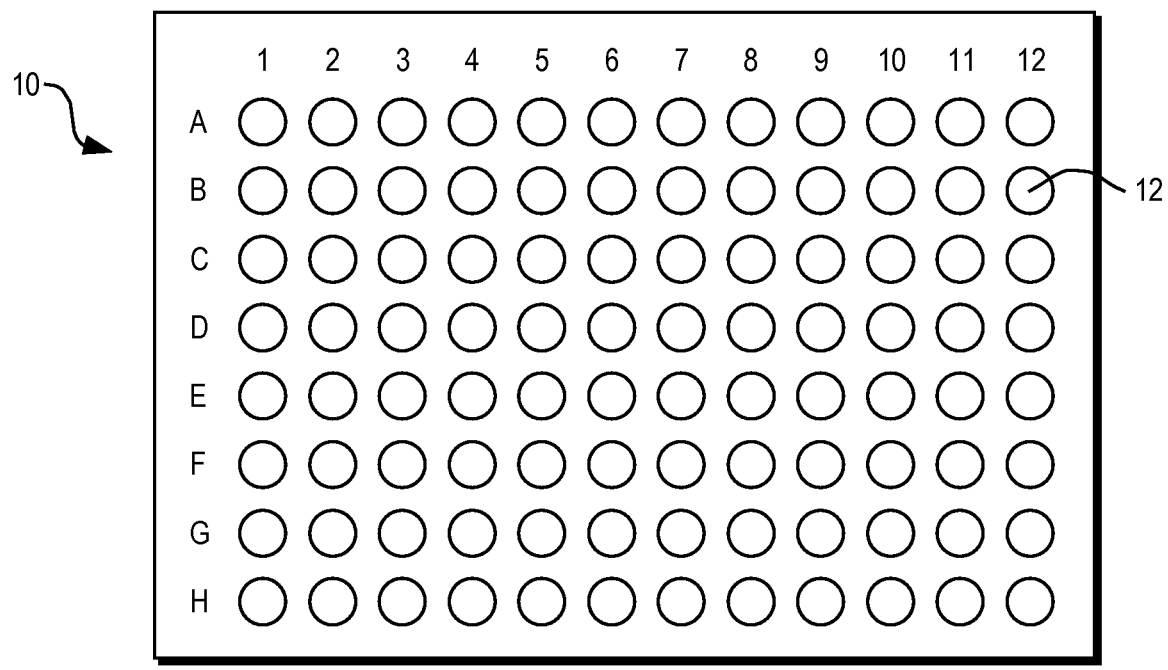
FIG. 1A shows a multi-well plate device of the present invention.
Figure 1B:
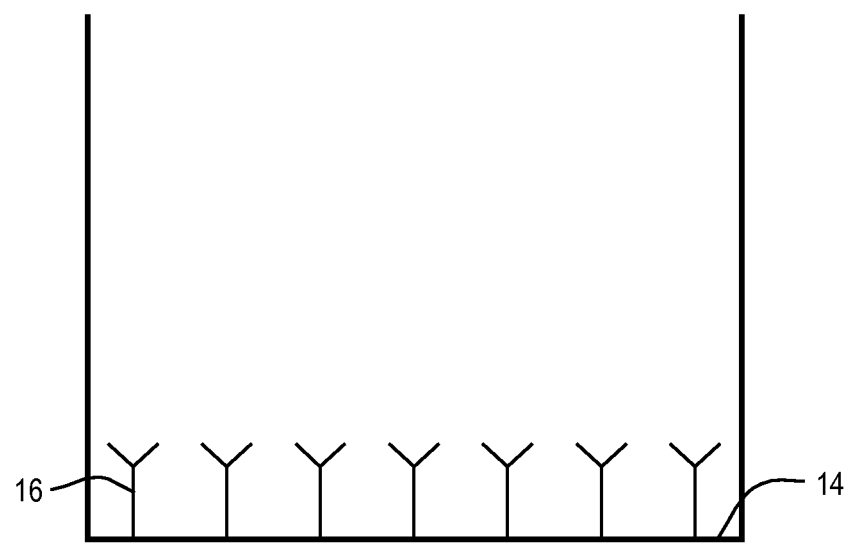
FIG. 1B shows a close up of a single well of the plate of FIG. 1A with an example representation of antibodies immobilized thereto.

As shown in FIGS. 1A and 1B, the device of the present invention is, for example, a multi-well plate 10 including a plurality of wells 12. Each well 12 provides a solid support 14 for immobilizing thereon anti-Ac-ASP-5 pAB 16. The plate 10 may be an Immulon 1B 96-well plate, but is not limited thereto.

Anti-Ac-ASP-5 pAB 16 is immobilized onto the solid support 14 of the well 12 of the plate 10 by physical adsorption. Immobilization of anti-Ac-ASP-5 pAB 16 onto the solid support 14 is performed so that anti-Ac-ASP-5 pAB 16 will not be washed away by wash procedures that may be performed, and so that the specific binding of coproantigens to anti-Ac-ASP-5 pAB 16 is unimpeded by the solid support 14 or other device surface while the method of the present invention is being performed. The device 10 of the present invention is suitable for detecting hookworm antigen by the method of the present invention, which may include performing an ELISA assay.

The method of the invention may be used to detect one or more hookworm antigens in a sample. The test sample used in the method of the invention is a fecal sample. The method of invention may be used to test a fecal sample from any animal, such as a canine or a feline.

The device 10 of the present invention, which includes anti-Ac-ASP-5 pAB 16 immobilized on the solid support 14, may be used in conjunction with a method of the present invention to detect hookworm in the fecal sample. Specifically, an active hookworm infection of an animal may be diagnosed by detecting one or more hookworm coproantigens with anti-Ac-ASP-5 pAB 16 that is immobilized on the solid support 14 of the device 10. "Hookworm coproantigens" are any hookworm components present in a fecal sample (e.g., the soluble fraction of a fecal sample) that can specifically and stably bind to anti-Ac-ASP-5 pAB 16. Hookworm coproantigens therefore may be whole hookworm, hookworm fragments, products secreted, excreted or shed from hookworm or a combination thereof.

"Specific for" or "stably binds" means that anti-Ac-ASP-5 pAB 16 recognizes and binds to hookworm coproantigens with greater affinity than to other coproantigens (e.g., coproantigens from one or more of roundworm, whipworm, tapeworm and heartworm). Binding specificity can be tested using methodology well known in the art, for example, ELISA, western blotting, or a radioimmunoassay (RIA).

In one aspect of the method of the present invention, hookworm antigen is detected by ELISA. It is to be understood that the ELISA in the method of the present invention may be performed according to any variation of the ELISA method known in the art. In one aspect of the method of the present invention, a fecal sample prepared as described as follows is added to one of the wells 12 of the plate 10 containing immobilized anti-Ac-ASP-5 pAB 16. Any antigen present in the fecal sample that is specific to anti-Ac-ASP-5 pAB 16 is allowed to specifically bind to the immobilized anti-Ac-ASP-5 pAB 16. Free anti-Ac-ASP-5 pAB is labeled, such as with horseradish peroxidase (HRP) by using the crosslinker succinimidyl 4-[N-maleimidomethyl]cyclohexane-1-carboxylate (SMCC), for example, to create a conjugate that is capable of specifically binding to the antigen that is specifically bound to the immobilized anti-Ac-ASP-5 pAB 16. After the addition of an enzyme substrate-chromogen reagent, the labeled anti-Ac-ASP-5 pAB bound to the immobilized anti-Ac-ASP-5 pAB 16 is detected by spectrophotometry. In this arrangement, the optical density (OD) value obtained for any particular well 12 of the 96-well plate 10 is directly proportional to the amount of specifically bound antigen present in the well. A specific example of the ELISA method of the present invention follows.

The method of the present invention is more specifically described with reference to an Example, which includes four Experiments; however, it is not to be construed as being limited thereto.

Example

The following materials and methods were used to generate data described in Experiments 1-4 described below.

Infection and anti-helminth treatment of canine animals. For Experiments 1 and 2, parasitic nematode infection was effected by orally administering about 150-300 larvated eggs of either hookworm, roundworm, or whipworm to a healthy beagle canine, which was raised on a controlled diet throughout Experiments 1 and 2. Further, for Experiment 2 only, canines were treated at post-infection day 91 with Interceptor®, which is an anthelmintic agent commercially available from Novartis Animal Health Inc. of Basel, Switzerland, according to the manufacturer's protocol. It is well known by those of ordinary skill in the art that Interceptor® is effective for the removal of parasitic nematodes from canine animals. For Experiments 3 and 4, canine animals were not artificially infected as described for Experiments 1 and 2, but instead were those which developed infection to hookworm, roundworm, whipworm, tapeworm or heartworm naturally. (Fecal samples obtained from canine animals having a naturally-derived worm infection are hereinafter referred to as being "field" fecal samples.) Unlike the beagle canine animals of Experiments 1 and 2, all of which were raised under the same controlled conditions, the canine animals of Experiments 3 and 4 were of varying breeds and were not raised under the same controlled conditions (e.g., their diets varied). Also, since these animals developed infection naturally, it is unknown which day post-infection that the field fecal samples obtained from these animals were taken. In all cases but for heartworm, infection was confirmed by microscopic observation of worm eggs in fecal samples obtained from the canine animals. When microscopic detection of eggs was used as the method of diagnosing infection, canines producing fecal samples that were free of worm eggs were considered to be uninfected. Heartworm infection was confirmed by using the SNAP® Heartworm Antigen Test Kit, which is commercially available from IDEXX Laboratories, Inc. of Westbrook, Me., according to the manufacturer's recommended protocol.

Anti-Ac-ASP-5 Antibody. The *Ancylostoma caninum* ASP-5 protein (Accession No. AY217006; Zhan et al. (Int. J. Parisitol. (2003), vol. 33, p. 897) was expressed as a full-length protein without the N-terminal signal sequence, and purified according to standard methods known in the art. The purified ASP-5 protein was used to immunize rabbits, according to standard methods know in the art, to produce rabbit anti-Ac-ASP-5 antiserum. IgG antibody was isolated from the rabbit anti-Ac-ASP-5 antiserum, using protein G purification according to methods well known in the art, to produce anti-Ac-ASP-5 pAB.

ELISA assays. Protein G purified rabbit anti-Ac-ASP-5 pAB (5 µg/ml; 100 µl/well) was immobilized by physical adsorption on Immulon 1B 96-well plates overnight at 4° C. The plates were then blocked with 1% BSA in 0.1M Tris pH 7.0 at 4° C. overnight, followed by drying at room temperature. Approximately 100 µl of fecal extract was added to each well and allowed to incubate at room temperature for one hour. Fecal extract was prepared by suspending 1 g of solid fecal material into 4 ml of diluent solution ("diluent solution" is 0.05 M Tris base; 1 mM EDTA; 0.45% Kathon; 16 mg/ml gentamicin sulfate; 0.05% Tween-20; 40% fetal bovine serum; 10% rabbit serum; and 5% mouse serum). The suspension was centrifuged at 4000 rpm for 20 minutes to produce a first supernatant. The first supernatant was centrifuged at 12000 rpm for 5 minutes to produce a second supernatant, which is referred to herein as "fecal extract". The wells were washed five times with a PBS-Tween-20 solution according to standard methods known to those of ordinary skill in the art. In a separate process, the protein G purified rabbit anti-Ac-ASP-5 pAB was labeled with HRP by using (SMCC) to create a conjugate. 1-10 µg/ml of this conjugate was added to each well of the 96-well plate. Following a 30' incubation period at room temperature, unbound conjugate was washed from the wells using PBS-Tween-20 solution according to standard methods known to those of ordinary skill in the art. 50 µl TMBLUE® peroxidase substrate (SeraCare Life Sciences, West Bridgewater, Mass.) was then added to each well according to standard methods known to those of ordinary skill in the art, and the plates were incubated for 10' at room temperature. After stopping each enzymatic reaction with 0.1% sodium dodecyl sulfate (SDS) following the 10' incubation period, the OD value of each well of the 96-well plate was measured at A650 by standard spectrophotometric techniques by using an ELISA plate reader.

Experiment 1

Anti-Ac-ASP-5 pAB specifically binds hookworm canine coproantigens.

Figure 2:
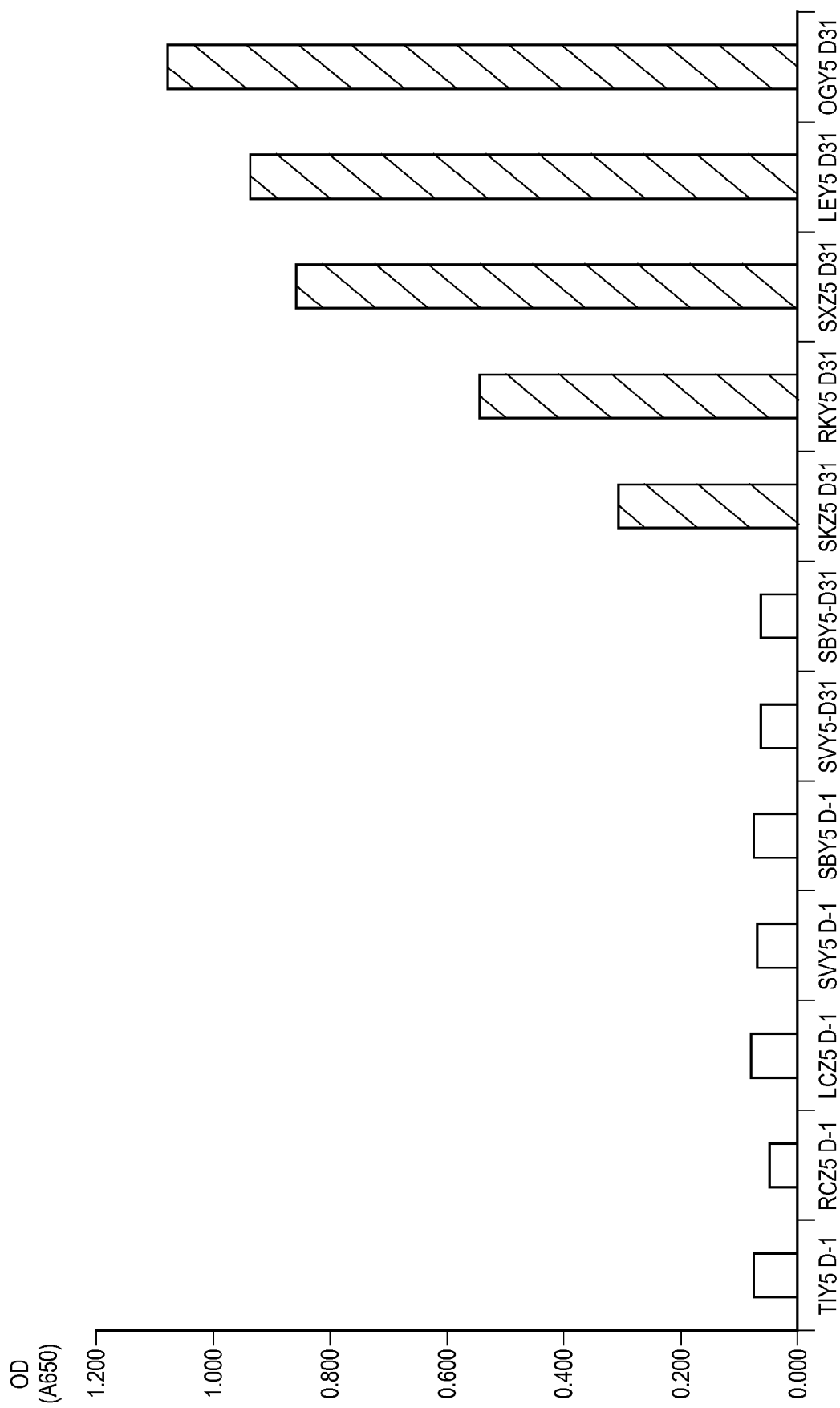
FIG. 2 shows a graph of optical density (OD) values obtained from fecal samples of uninfected canines and hookworm-infected canines by following a method of the present invention in a first experiment.

It was a goal of Experiment 1 to determine whether anti-Ac-ASP-5 pAB specifically binds hookworm coproantigens. Single OD determinations for 12 canine fecal samples obtained in Experiment 1 are shown in FIG. 2. These fecal samples were obtained from five canine animals known to be free of parasitic worm infection (TIY5, RCZ5, LCZ5, SVY5, and SBY5), and five canine animals known to be infected with hookworm (SKZ5, RKY5, SXZ5, LEY5, and OGY5). Specifically, fecal samples were obtained on post-infection day 31 ("D31") for each of the five hookworm-infected canines. Fecal samples were obtained from each of the uninfected canines one day prior to infection of the hookworm-infected canines ("D-1"), and fecal samples were further obtained from two of the uninfected canines, SVY5 and SBY5, 31 days ("D31") after the infection of the hookworm-infected canines. Microscopic observation of the fecal samples tested in Experiment 1 showed that hookworm ova were substantially present in all five hookworm-infected canines, but were not present in any of the fecal samples taken from the uninfected canines.

The OD values measured of each of the two uninfected fecal samples at post-infection day 31 was 0.063. Conversely, the average OD measured of the five hookworm-infected fecal samples at post-infection day 31 was 0.750 (the OD values of these samples ranged from 0.309 to 1.083), which was about 12-fold higher than the 0.063 OD value measured for each of the uninfected samples. These data indicate that anti-Ac-ASP-5 pAB specifically binds one or more coproantigens in hookworm-infected canine animals, but does not specifically bind any coproantigen in uninfected canine animals. These data therefore indicate that anti-Ac-ASP-5 pAB can be used to detect the presence or absence of hookworm infection in a canine animal.

Experiment 2

Anti-Ac-ASP-5 pAB detects hookworm coproantigens as early as between nine days and 13 days after introduction of hookworm infection to the canine; anti-Ac-ASP-5 pAB detects hookworm coproantigens only at those times when the canine animal has an active hookworm infection; and anti-Ac-ASP-5 pAB does not specifically bind coproantigens from roundworm or whipworm.

It was one goal of Experiment 2 to determine how soon after infection anti-Ac-ASP-5 pAB is able to detect hookworm coproantigens compared to the above-mentioned gold-standard fecal floatation method. Further, it was a second goal of Experiment 2 to determine whether anti-Ac-ASP-5 pAB detects hookworm infection in an animal only at appropriate times (that is, only when an animal has an active hookworm infection). Even further, it was a third goal of Experiment 2 to determine whether anti-Ac-ASP-5 pAB detects coproantigens from roundworm and/or whipworm.

Figure 3:
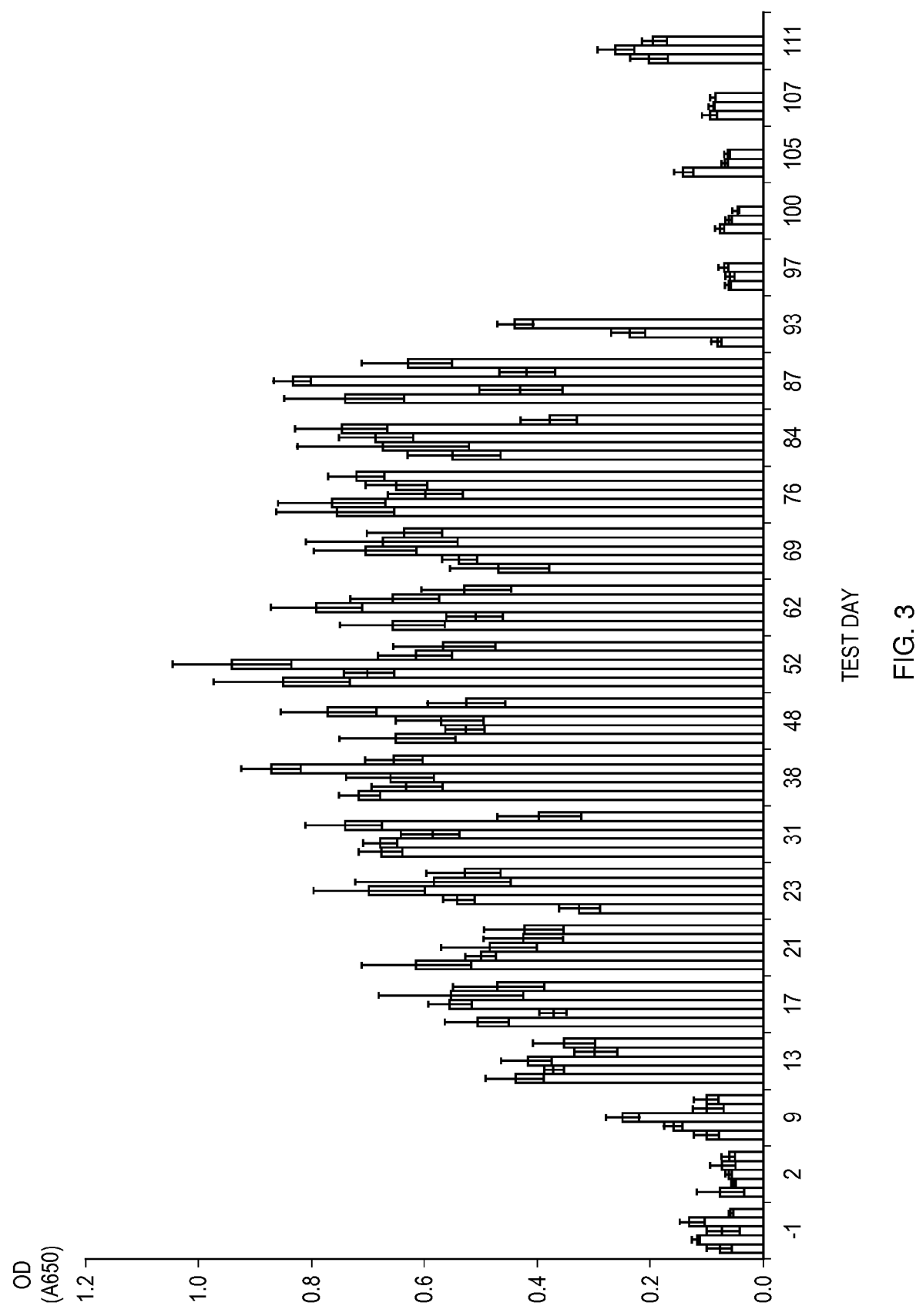
FIG. 3 shows a first graph of OD values obtained from fecal samples of hookworm-infected canines by following a method of the present invention in a second experiment.
Figure 4:
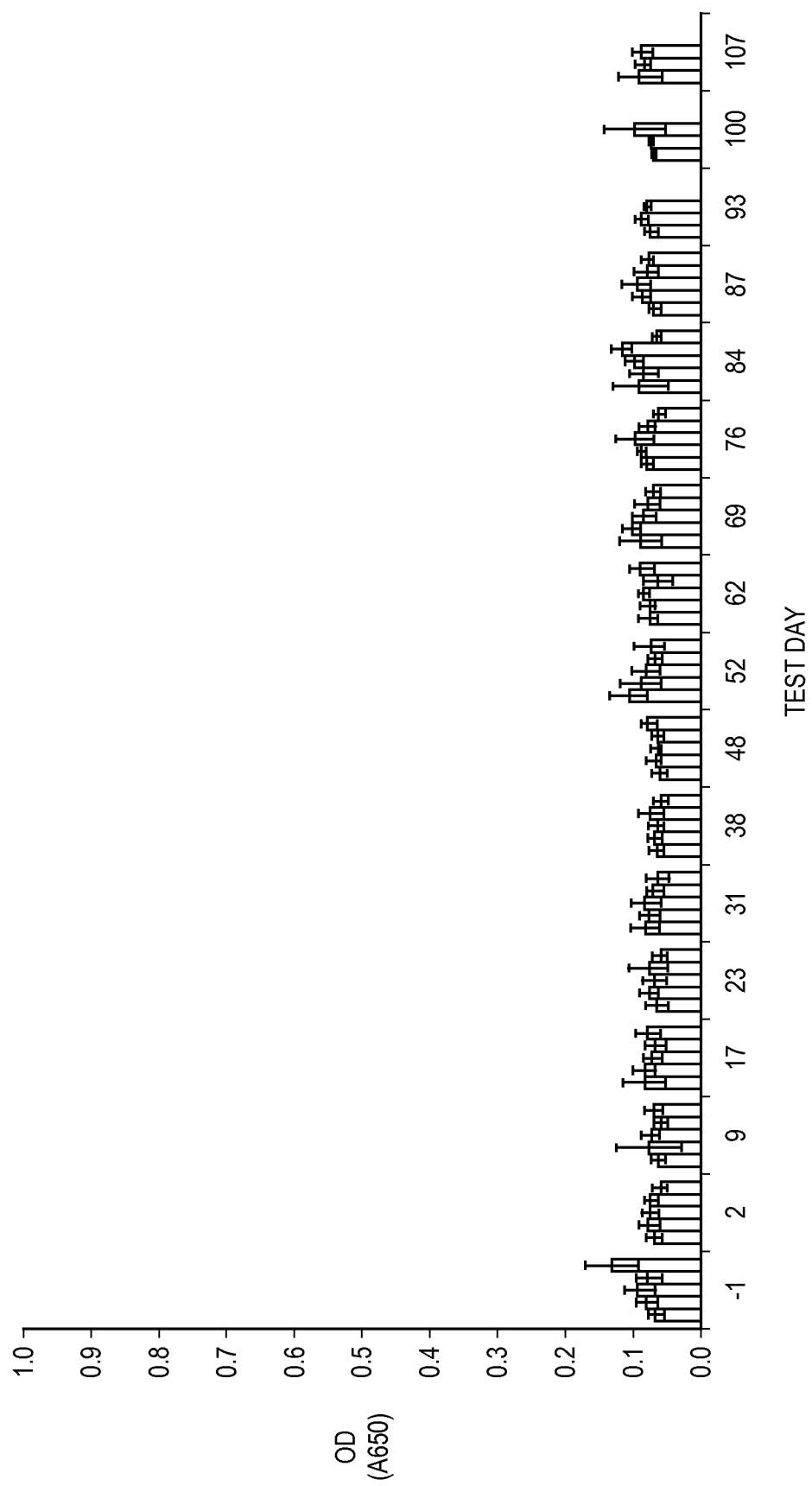
FIG. 4 shows a second graph of OD values obtained from fecal samples of uninfected canines by following a method of the present invention in the second experiment.

OD values measured for fecal samples obtained from hookworm-infected canines and uninfected canines are shown in FIGS. 3 and 4, respectively. Specifically, FIG. 3 shows average OD values (and standard deviations) generated using fecal samples taken from hookworm-infected canines over the course of 112 days. (Each OD value shown in FIG. 3 is the average of six OD values generated from the same fecal sample in six separate ELISA reactions.) Data from the same five canine animals are shown for days −1 (i.e., one day before administration of hookworm infection to the animals) and 87, and for selected days therebetween. Data from three of these five canines are shown for days 93 and 111, and for selected days therebetween.

FIG. 4 shows average OD values (and standard deviations) measured using fecal samples from uninfected canines over the course of 108 days. (Each OD value shown in FIG. 4 is the average of six OD values obtained from the same fecal sample in six separate ELISA reactions.) Data from the same five uninfected canines are shown for days −1 (i.e., one day before administration of hookworm infection to the hookworm-infected animals) and 87 and for selected days therebetween. Data from three of these five canines are shown for each of days 93, 100 and 107.

Referring to FIG. 3, the average of the average OD values measured for the hookworm-infected canines was 0.067 on post-infection day 2 (as shown in FIG. 4, the average of the average OD values measured for the uninfected animals on that same day was 0.068). On post-infection day 9, the average of the average OD value measured for the hookworm-infected canines increased to 0.143, which was more than two-fold higher than the average of the average OD values measured for the uninfected animals on that same day (0.066; see FIG. 4). On post-infection day 13, the average of the average OD values measured for the hookworm-infected canines increased to 0.379, which was more than five-fold higher than the average of the average OD values measured for the uninfected canine animals on day 9 (0.066; see FIG. 4) and day 17 (0.075; see FIG. 4). Further, hookworm ova first appeared in the fecal samples obtained from the hookworm-infected canine animals on post-infection day 17. Experiment 2 therefore indicates that anti-Ac-ASP-5 pAB detected hookworm coproantigens in hookworm-infected canine animals as early as between nine days and 13 days post-infection, and therefore detected these coproantigens at least four days before hookworm ova first appeared in the feces of the hookworm-infected canines.

For post-infection days 13 to 87, the average OD values generated from the hookworm-infected canine animals were several-fold higher than were the average OD values generated from the uninfected animals during that same period. (For each test day during that period, the average of the average OD value measured for the hookworm-infected canines was 0.496 or greater, whereas the average of the average OD values measured for the uninfected animals was 0.093 or less.) This result was consistent with the results obtained in Experiment 1 and further support the Experiment 1 conclusion that anti-Ac-ASP-5 pAB can be used to the presence or absence of hookworm infection in a canine animal.

Microscopic observation of the fecal sample taken from the hookworm-infected canine animals on post-infection day 93 showed that the sample was moderately free of hookworm ova, and microscopic observation of the fecal samples taken from the hookworm-infected animals on post-infection days 97 and thereafter showed that the samples were substantially free of hookworm ova. It is expected that the moderate reduction in ova on post-infection day 93 and the substantial reduction in ova on post-infection day 97 and thereafter was due to the anthelmintic treatment administered on post-infection day 91. Referring to FIG. 3, the average of the average OD values measured for the hookworm-infected canines was consistent with the observed reduction of ova number in the fecal samples taken from these animals. Specifically, the average of the average OD value measured for these canines on the days following anthelmintic treatment ranged from 0.70 to 0.260. (The largest average OD value, that is, the 0.260 value, was measured for the post-infection day 93 fecal samples, which were taken only two days after the administration of the anthelmintic when a moderate amount of ova were still present in the feces.) These values were several-fold less than the average of the average OD values measured on post-infection day 87 (0.619), which was the last day on which fecal samples were tested prior to anthelmintic administration. The average of the average OD values measured for the uninfected canine animals over this same period were 0.082 or less.

Experiment 2 therefore further indicates that anti-Ac-ASP-5 pAB robustly detected hookworm coproantigens when a host animal was substantially infected with hookworm, weakly detected hookworm coproantigens when a host animal was moderately infected with hookworm, and did not detect hookworm coproantigens when a host animal was substantially free of hookworm infection.

Figure 5:
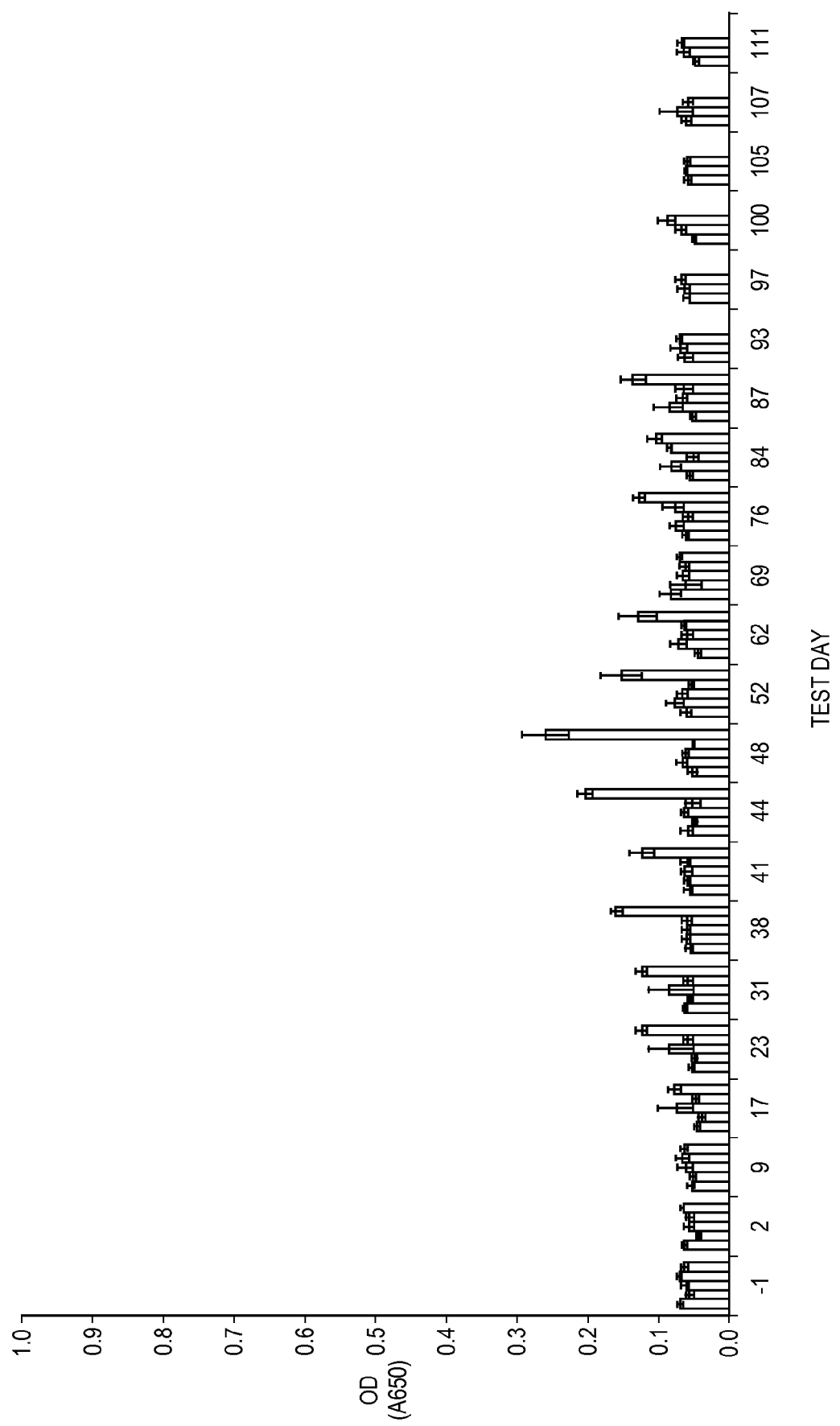
FIG. 5 shows a third graph of OD values obtained from fecal samples of roundworm-infected canines by following a method of the present invention in the second experiment.
Figure 6:
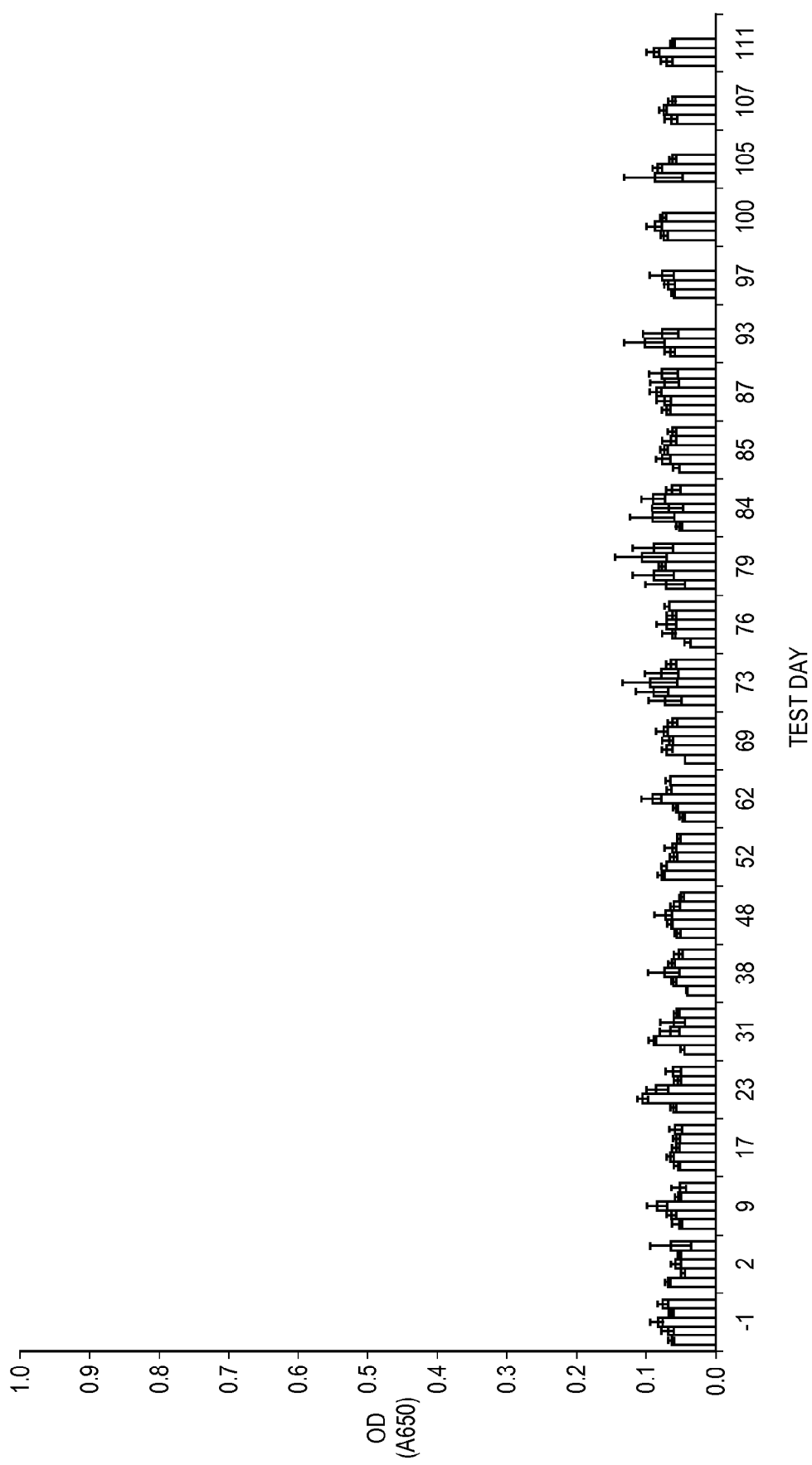
FIG. 6 shows a fourth graph of OD values obtained from fecal samples of whipworm-infected canines by following a method of the present invention in the second experiment.

OD determinations for fecal samples obtained from roundworm-infected canine animals and whipworm-infected canine animals are shown in FIGS. 5 and 6, respectively. Specifically, FIG. 5 shows average OD values (and standard deviations) generated using fecal samples taken from roundworm-infected canines over the course of 112 days, and FIG. 6 shows average OD values (and standard deviations) generated using fecal samples taken from whipworm-infected canines over the course of 112 days. (In FIGS. 5 and 6, each OD value shown is the average of six OD values generated from the same sample.) Data from the same five roundworm-infected canines and from the same five whipworm-infected canines are shown for days −1 (i.e., one day before administration of hookworm infection to the animals) and 87, and for selected days therebetween. Data from three of the five roundworm-infected canines and from three of the five whipworm-infected canines are shown for days 93 and 111, and for selected days therebetween.

With continuing reference to FIGS. 5 and 6, the average of the average OD values measured for the roundworm-infected and whipworm-infected canines was consistently 0.102 or less for the roundworm-infected canines and less than 0.100 for the whipworm-infected canines throughout the test period. In each case, these values are several-fold less than the average of the average OD values measured for the hookworm-infected canines over the corresponding period.

These data indicate that anti-Ac-ASP-5 pAB does not specifically bind any coproantigen in roundworm-infected or whipworm-infected canines. Therefore, anti-Ac-ASP-5 pAB may be used to confirm the presence or absence of hookworm infection in a canine animal regardless of whether that animal is infected with either or both of roundworm and whipworm.

Experiment 3

Anti-Ac-ASP-5 pAB does not specifically bind tapeworm coproantigen and anti-Ac-ASP-5 pAB binds hookworm in field fecal samples.

Figure 7:
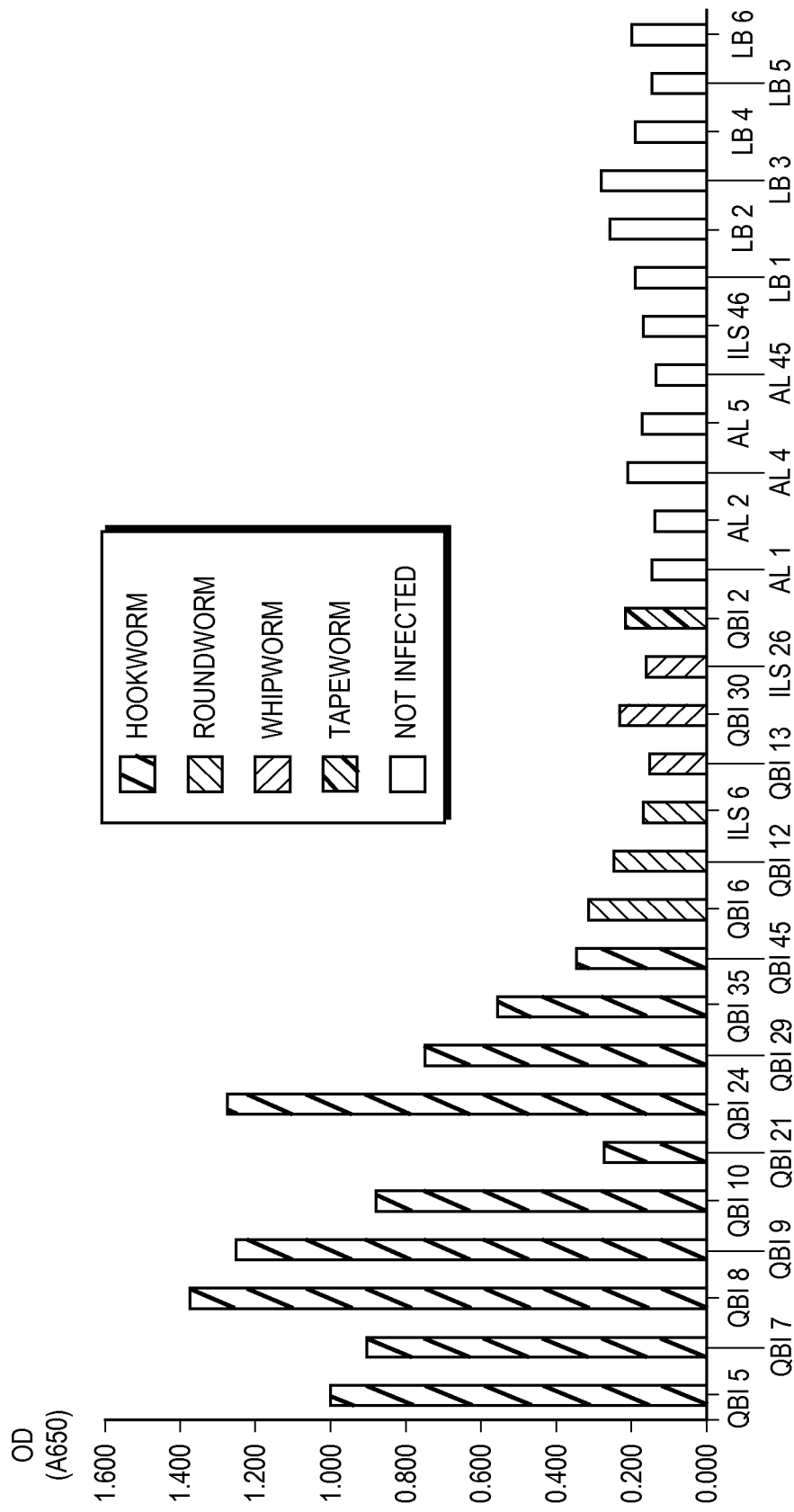
FIG. 7 shows a graph of OD values obtained from fecal samples of uninfected canines and canines infected with either hookworm, roundworm, whipworm or tapeworm by following a method of the present invention in a third experiment.

It was a goal of Experiment 3 to determine whether anti-Ac-ASP-5 pAB specifically binds tapeworm coproantigen. It was a second goal of Experiment 3 to determine whether anti-Ac-ASP-5 pAB specifically binds coproantigen of one or more of hookworm, roundworm, whipworm and tapeworm in field canine fecal samples. Single OD determinations for field fecal samples obtained from hookworm-infected, roundworm-infected, whipworm-infected, tapeworm-infected, and uninfected canine animals are shown in FIG. 7. The OD values measured for the hookworm-infected canine animals, which averaged 0.871 (and ranged from 0.274 to 1.388), were several-fold higher than were the OD values measured for the roundworm-infected, whipworm-infected, and uninfected canine animals. Specifically, the average OD value measured for the roundworm-infected canine animals was 0.241, the average OD value measured for the whipworm-infected canine animals was 0.180, and the average OD value measured for the uninfected canine animals was 0.184. Further, the OD values measured for the hookworm-infected canine animals were more than four-fold higher than was the OD value generated for the tapeworm-infected canine included in this Experiment (specifically, the OD value of the tapeworm-infected canine animal was 0.217).

These data further support the conclusion that anti-Ac-ASP-5 pAB does not specifically bind any coproantigen in roundworm-infected canine animals or whipworm-infected canine animals. These data also indicate that anti-Ac-ASP-5 pAB does not specifically bind any tapeworm coproantigen. These data further indicate that anti-Ac-ASP-5 pAB specifically binds hookworm antigen in field fecal samples from hookworm-infected canine animals. The observation that anti-Ac-ASP-5 pAB specifically binds hookworm antigen in field fecal samples from hookworm-infected canine animals is significant because it confirms that anti-Ac-ASP-5 pAB is capable of detecting hookworm in fecal samples obtained from canines of varying breeds and of varying diets.

Experiment 4

Anti-Ac-ASP-5 pAB does not specifically bind heartworm coproantigen.

Figure 8:
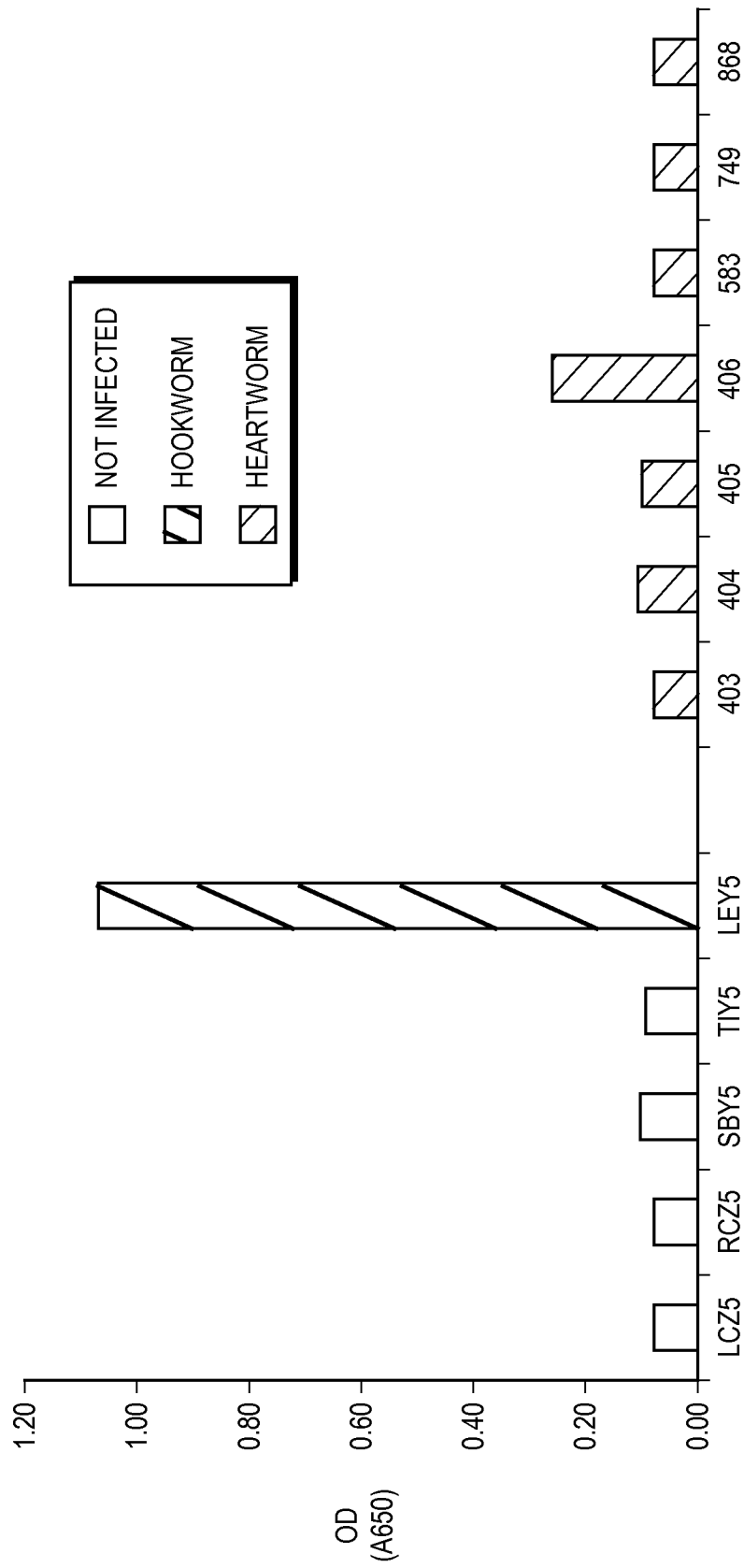
FIG. 8 shows a graph of OD values obtained from fecal samples of uninfected canines and canines infected with either hookworm or heartworm by following a method of the present invention in a fourth experiment.

It was a goal of Experiment 4 to determine whether anti-Ac-ASP-5 pAB specifically binds heartworm coproantigen. OD determinations for 11 canine field fecal samples are shown in FIG. 8. Specifically, FIG. 8 shows single OD values measured for fecal samples from four canine animals known to be free of parasitic worm infection (LCZ5, RCZ5, SBY5, and TIY5), one canine animal known to be infected with hookworm (LEY5), and seven canine animals known to be infected with heartworm (403, 404, 405, 406, 583, 749 and 868).

The average OD value measured for the uninfected samples was 0.090 (with a range of 0.077 to 0.109), whereas the average OD value obtained from the heartworm-infected samples was 0.125 (with a range of 0.88 to 0.267). The lone OD value measured for the hookworm-infected canine was 1.074, which was more than 10-fold higher than the average OD value measured for the uninfected samples and almost nine-fold higher than the average OD value measured for the heartworm-infected samples, and is consistent with other OD values obtained for hookworm-infected samples described herein. Taken together, these data support the conclusion that anti-Ac-ASP-5 pAB specifically binds coproantigens in hookworm-infected fecal samples, does not specifically bind coproantigen in uninfected fecal samples, and further show that anti-Ac-ASP-5 pAB does not specifically bind heartworm coproantigens. Additionally, these data further confirm that anti-Ac-ASP-5 pAB specifically binds hookworm antigen in field fecal samples from hookworm-infected canine animals.

While the devices, methods and kits of the present invention have been described with respect to a specific embodiment and a specific Example, it is to be understood that variations to the device and/or the method of the present invention may be made without departing from the spirit and scope of the invention. For example, whereas anti-Ac-ASP-5 pAB was raised in rabbit against purified recombinant ASP5, polyclonal antibody also may be raised in, for example, a human or other primate, mouse, rat, guinea pig, goat, pig, cow, sheep, donkey, dog, cat, chicken, or horse. An antibody used in the invention also may be any antibody class, including for example, IgG, IgM, IgA, IgD and IgE. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al., *Methods Cell. Biol.* 37:7-56 (1993); Morrison, *Ann. Rev. Immunol.* 10:239-65 (1992); Wright et al., *Crit. Rev. Immunol.* 12:125-68 (1992). Further, it is to be understood that the polyclonal antibody need not be raised against recombinant ASP5. Therefore, the polyclonal antibody may be raised against naturally occurring ASP5. Methods for isolating naturally occurring proteins are well known in the art. See, e.g., Cutler, *Protein Isolation Protocols*, 2$^{nd}$ Ed., Humana Press (2003); Bollag et al., *Protein Methods*, 2$^{nd}$ Ed., Wiley-Liss Publishers (1996).

An antibody used in the devices, methods and kits of the invention can also be a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, F(ab')$_2$ and F$_v$ fragments.

Antibodies used in the devices, methods and kits of the invention may be immobilized on the solid support by any methodology known in the art, including, for example, covalently or non-covalently, directly or indirectly, attaching the antibodies to the solid support. Therefore, while anti-Ac-ASP-5 pAB is attached to the solid support by physical adsorption (i.e., without the use of chemical linkers) in the embodiment described, it is contemplated that anti-Ac-ASP-5 pAB or other antibodies may be immobilized to the solid support by any chemical binding (i.e., with the use of chemical linkers) method readily known to one of ordinary skill in the art.

The solid support of the device is not limited to being a polystyrene 96-well plate. The solid support may be any suitable material for the immobilization of antibodies specific for hookworm. For example, the solid support may be beads, particles, tubes, wells, probes, dipsticks, pipette tips, slides, fibers, membranes, papers, natural and modified celluloses, polyacrylamides, agaroses, glass, polypropylene, polyethylene, dextran, nylon, amylases, plastics, magnetite or any other suitable material readily known to one of ordinary skill in the art.

The device of the present invention may be one that is suitable for performing a lateral flow assay. An exemplary device that is useful for performing a lateral flow assay that is useful in the present invention is described in U.S. Pat. No. 5,726,010, which is incorporated herein by reference in its entirety. The device for performing a lateral flow assay therefore may be a SNAP® device, which is commercially available from IDEXX Laboratories, Inc. of Westbrook, Me.

The device may optionally include one or more labeled antigen capture reagents that may be mixed with a fecal sample prior to application to a device of the invention. When the labeled antigen reagent is included, the labeled antigen capture reagent may or may not be deposited or dried on the solid surface of the device. "Antigen capture" means any compound that is specific for the antigen of interest. The labeled antigen capture reagent, whether added to a fecal sample or pre-deposited on the device, may be, for example, a labeled antibody specific for a hookworm antigen. For example, a hookworm-specific antibody conjugated with horseradish peroxidase may be used as a labeled antigen capture reagent.

The device also may optionally include a liquid reagent that transports, such as when the device includes the SNAP® device, for example, or facilitates removal of, such as when the device includes a 96-well plate, for example, unbound material (e.g., unreacted fecal sample and unbound antigen capture reagent) away from the reaction zone (solid phase). The liquid reagent may be a wash reagent and serve only to remove unbound material from the reaction zone, or it may include a detector reagent and serve to both remove unbound material and facilitate antigen detection. For example, in the case of an antigen capture reagent conjugated to an enzyme, the detector reagent includes a substrate that produces a detectable signal upon reaction with the enzyme-antibody conjugate at the reaction zone (solid phase). Alternatively, in the case of a labeled antigen capture reagent conjugated to a radioactive, fluorescent, or light-absorbing molecule, the detector reagent acts merely as a wash solution facilitating detection of complex formation at the reactive zone by washing away unbound labeled reagent.

The liquid reagent may further include a limited quantity of an "inhibitor", i.e., a substance that blocks the development of the detectable end product. A limited quantity is defined as being an amount of inhibitor sufficient to block end product development until most or all excess unbound material is transported away from the second region, at which time detectable end product is produced.

The device of the present invention may also include various binding reagents immobilized at locations distinct from the antigen capture reagent(s). For example, an immunoreagent (an antibody, antigen or peptide) that recognizes a species-specific (e.g., worm-specific) antibody portion of a labeled antibody or antigen capture reagent or an enzyme portion of an enzyme-labeled reagent can be included as a positive control to assess the viability of the reagents within the device. For example, a positive control may be an anti-horseradish peroxidase antibody that has been raised in, for example, a goat or a mouse. Additionally, a reagent, e.g., an antibody, isolated from a non-immune member of the species from which the antibody portion of the antigen-antibody complex was derived can be included as a negative control to assess the specificity of immunocomplex (i.e., antigen-antibody complex) formation.

In addition to being designed to detect hookworm in a fecal sample, the device of the invention optionally may be designed to allow one or more other diagnostic tests to be performed. For example, the solid support may also include reagents for the detection of one or more non-hookworm worm parasites, one or more non-worm parasites, one or more viruses, or one or more bacteria. The reagents for the detection of one or more non-hookworm worm parasites, one or more non-worm parasites, one or more viruses or one or more bacteria may be, for example, one or more antibodies or one or more antigens recognized by antibodies specific for one or more non-hookworm worm parasites, one or more non-worm parasites, one or more viruses or one or more bacteria.

In the method of the present invention, detection of a hookworm infection is accomplished by detecting the presence or absence of one or more hookworm antigens in a fecal sample. The soluble portion of a fecal sample to be tested may be collected by any protocol known in art. For example, in addition to the specific protocol described above, the soluble portions of the sample may be collected using filtration, centrifugation, or simple mixing followed by gravimetric settling.

The method includes contacting the fecal sample with one or more antibodies specific for one or more hookworm antigens under conditions that allow an antigen/antibody complex, i.e., an immunocomplex, to form. That is, an antibody specifically binds to a hookworm antigen present in the fecal sample. One of ordinary skill in the art would be familiar with assays and conditions that are used to detect antigen/antibody complex binding. For example, the antigen/antibody complex may be detected using a secondary antibody that binds to the antigen/antibody complex. The formation of a complex between hookworm antigen and anti-hookworm antibodies in the sample may be detected using any suitable method known in the art. Further, the amount of antibody-antigen complexes can be determined by methodology known in the art. A level that is higher than that formed in a control sample indicates a hookworm infection.

Alternative steps of the method of the present invention may include applying the fecal sample to a device of the invention, which includes an immobilized antibody specific for hookworm antigen, and detecting the presence or absence of the hookworm antigen in the fecal sample. Antibodies specific for antigens of hookworm may be directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). All of these substrate materials may be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

The method of the present invention need not include the use of solid phases or substrates, however. For example, the methods may include immunoprecipitation methods which do not require the use of solid phases or substrates.

In some embodiments of the invention, the antigen/antibody complex is detected when an indicator reagent, such as an enzyme conjugate, which is bound to the antibody, catalyzes a detectable reaction. Optionally, an indicator reagent including a signal generating compound may be applied to the antigen/antibody complex under conditions that allow formation of a detectable antigen/antibody/indicator complex. Optionally, the antibody may be labeled with an indicator reagent prior to the formation of an antigen/antibody complex.

The formation of an antigen/antibody complex or an antigen/antibody/indicator complex in some of the methods of the present invention specifically may be detected by radiometric, colorimetric, fluorometric, size-separation, or precipitation methods. Detection of an antigen/antibody complex also may be accomplished by the addition of a secondary antibody that is coupled to an indicator reagent including a signal generating compound. Indicator reagents including signal generating compounds (labels) associated with a polypeptide/antibody complex may be detected using the methods described above and may include chromogenic agents, catalysts such as enzyme conjugates, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Antibodies, including secondary antibodies, may be labeled with any type of label known in the art, including, for example, fluorescent, chemiluminescent, radioactive, enzymes, colloidal particles, radioisotopes and bioluminescent labels. In various embodiments of the invention, the one or more of the antibodies of the invention are labeled with an enzyme, a colloidal particle, a radionuclide or a fluorophor. The particulate label can be, for example, a colored latex particle, dye sol, or gold sol conjugated to an antibody specific for a hookworm antigen.

Methods of the invention include, but are not limited to those based on competition, direct reaction or sandwich-type assays, including, but not limited to ELISA, western blots, RIA, immuno-fluorescent assays (IFA), hemagglutination (HA), fluorescence polarization immunoassay (FPIA), and microtiter plate assays (any assay done in one or more wells of a microtiter plate). One assay of the invention includes a reversible flow chromatographic binding assay, which may be performed, for example, by using a SNAP® device. See U.S. Pat. No. 5,726,010.

Methods of the invention facilitate sandwich or competition-type specific binding assays. In a sandwich assay, antigen capture reagents are immobilized in a reactive zone. These antigen capture reagents may specifically bind to antigens in the fecal sample being tested. Specifically, these antigen capture reagents specifically bind to an antigen from a hookworm, if present in the fecal sample. Following binding of the antigen from the sample, the antigen capture reagent/antigen complex is detected by any suitable method. For example, the complex may be reacted with labeled specific binding reagents (e.g., an enzyme-antibody conjugate) and antigen detected (e.g., upon reaction with substrate).

In other embodiments of the method of the present invention, a competition assay is performed. In a competition assay, antigen capture reagents are immobilized at the reactive zone and are contacted simultaneously with antigen from a sample and labeled antigen (e.g., an antigen-enzyme conjugate). The amount of label detected at the reactive zone is inversely proportional to the amount of antigen in the sample.

In some embodiments of the invention, antibodies specific for a hookworm antigen or antigens are attached to a solid phase or substrate. The fecal sample potentially including an antigen from hookworm is added to the substrate. Antibodies that specifically bind hookworm are added. The antibodies may be the same antibodies used on the solid phase or they may be from a different source or species. Further, these antibodies may be linked to an indicator reagent, such as an enzyme conjugate. Wash steps may be performed prior to each addition. A chromophore or enzyme substrate may be added and color may be allowed to develop. The color reaction may be stopped and the color may be quantified using, for example, a spectrophotometer.

In other embodiments of the invention, antibodies specific for a hookworm antigen or antigens are attached to a solid phase or substrate. A fecal sample potentially including a hookworm antigen is added to the substrate. Second antibodies that specifically bind antigens of hookworms are then added. These second antibodies may or may not be from a different species than are the solid phase antibodies. Third anti-species antibodies that specifically bind the second antibodies and that do not specifically bind the solid phase antibodies are then added. The third antibodies may include an indicator reagent, such as an enzyme conjugate. Wash steps may be performed prior to each addition. A chromophore or enzyme substrate may added and color may be allowed to develop. The color reaction may be stopped and the color may be quantified using, for example, a spectrophotometer.

In a specific example, the method of the present invention is performed in conjunction with a device that is a lateral flow assay device by adding a prepared fecal sample to a flow matrix of the device at a first region (a sample application zone). The prepared fecal sample is carried in a fluid flow path by capillary action to a second region of the flow matrix where a particulate label capable of binding and forming a first complex with an antigen in the fecal sample. The particulate label can be, e.g., a colored latex particle, dye sol, or gold sol conjugated to an antibody specific for a hookworm antigen. The first complex is carried to a third region of the flow matrix where an antibody that specifically binds a hookworm antigen is immobilized at a distinct location. A second complex is formed between the immobilized antibody and the first complex. The particulate label that is part of the second complex can be directly visualized.

Hookworm antibody may be an immobilized antigen capture reagent in a reaction zone (solid phase). A second antigen capture reagent, i.e., a second hookworm antibody that has been conjugated to a label, either may be added to the sample before the sample is added to the device, or the second antigen capture reagent can be incorporated into the device. For example, the labeled antigen capture reagent may be deposited and dried on a fluid flow path that provides fluid communication between a sample application zone and the solid phase. Contact of the labeled antigen capture reagent with the test sample can result in dissolution of the labeled antigen capture reagent.

The invention further includes assay kits (e.g., articles of manufacture) for detecting hookworm in a fecal sample. A kit therefore may include one or more devices of the present invention. For example, the kit may include anti-hookworm antibodies and means for determining binding of the antibodies to hookworm antigens in the sample. In one particular example, such a kit includes the device having an immobilized anti-hookworm antibody, one or more antigen capture reagents (e.g., a non-immobilized labeled antigen capture reagent and an immobilized antigen capture reagent) and wash reagent, as well as detector reagent and positive and negative control reagents, if desired or appropriate. Other components such as buffers, controls, and the like, known to those of ordinary skill in art, may be included in such test kits. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample. The antibodies, assays, and kits of the invention are useful, for example, in the diagnosis of individual cases of hookworm infection in a patient, as well as epidemiological studies of hookworm outbreaks. The kit may further include instructions for carrying out one or more methods of the present invention, including instructions for using any device of the present invention that is included with the kit.

The methods of the invention for detection of hookworm infection can be combined with other diagnostic assays to detect the presence of other organisms or conditions. For example, assays of the invention can be combined with reagents that detect one or more non-hookworm worm fecal parasites, one or more non-worm fecal parasites one or more viruses, one or more bacteria, one or more blood-borne parasites or occult blood or a combination thereof. By providing two or more unique binding sites in a single assay device (such as, for example, two unique spots on a SNAP® assay device), the present invention allows for detection of two or more organisms from a single sample. In one embodiment, there are three unique spots for detection of past or present infection from three organisms (the spots being either antigen or antibody binding reagents) from a single sample (i.e., the same, single sample is presented to the three capture reagents on a single device).

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

A number of examples to help illustrate the invention have been described. Nevertheless, it will be understood that various modifications may be made without departing from the spirit and scope of the invention. Accordingly, other embodiments are within the scope of the claims appended hereto.

What is claimed is:

1. A method of detecting the presence or absence of hookworm antigen in a fecal sample of a mammal comprising:
   (a) contacting the sample with one or more antibodies specific for *Ancylostoma caninum Ancylostoma*-secreted protein-5 (ASP5); and
   (b) detecting the presence or absence of one or more hookworm antigens or one or more hookworm antibody/antigen complexes.

2. The method of claim 1 wherein the one or more antibodies are polyclonal.

3. The method of claim 1 wherein the fecal sample is substantially free of hookworm ova based on microscopic observation, and the fecal sample is excreted by the mammal after the mammal is infected with hookworm.

4. The method of claim 1 wherein the fecal sample is excreted by the mammal no more than 13 days after the mammal has become infected with hookworm.

5. The method of claim 1 wherein the one or more antibodies specific for *Ancylostoma caninum* ASP5 are not capable of detecting any coproantigen derived from the group consisting of roundworm, whipworm, tapeworm and heartworm.

6. The method of claim 1 wherein the detecting the presence or absence of one or more antibody/antigen complexes includes the step of providing a secondary antibody that binds to the one or more antibody/antigen complexes.

7. The method of claim 6 wherein the secondary antibody is labeled.

8. The method of claim 1 wherein one or more of the one or more antibodies are labeled.

9. The method of claim 1 wherein the one or more antibodies are immobilized on a solid support.

10. The method of claim 9 wherein the solid support forms part of an enzyme-linked immunosorbent assay device.

11. The method of claim 10 wherein the enzyme-linked immunosorbent assay device is a lateral flow immunoassay device.

12. The method of claim 1 further comprising the step of applying the sample to one or more reagents to detect one or more of the group consisting of: one or more non-hookworm worm parasites, one or more non-worm parasites, one or more viruses, and one or more bacteria.

13. The method of claim 12 wherein the reagents for the detection of any one or all of the one or more non-hookworm worm parasites, the one or more non-worm parasites, the one or more viruses and the one or more bacteria are one or more antibodies or one or more antigens recognized by antibodies specific for the one or more non-hookworm worm parasites, the one or more non-worm parasites, the one or more viruses or the one or more bacteria.

* * * * *